United States Patent
Gottumukkala et al.

(10) Patent No.: US 10,017,515 B2
(45) Date of Patent: Jul. 10, 2018

(54) STABLE AMORPHOUS TICAGRELOR AND A PROCESS FOR ITS PREPARATION

(71) Applicant: Sun Pharmaceutical Industries Limited, Mumbai, Maharashtra (IN)

(72) Inventors: Nagaraju Gottumukkala, West Godavari (IN); Anil Saini, Rewari (IN); Ram Thaimattam, Hyderabad (IN); Mahavir Singh Khanna, New Delhi (IN); Mohan Prasad, Gurgaon (IN)

(73) Assignee: Sun Pharmaceutical Industries Limited, Mumbai (IN)

( * ) Notice: Subject to any disclaimer, the term of this patent is extended or adjusted under 35 U.S.C. 154(b) by 0 days.

(21) Appl. No.: 15/503,003

(22) PCT Filed: Aug. 11, 2015

(86) PCT No.: PCT/IB2015/056117
§ 371 (c)(1),
(2) Date: Feb. 9, 2017

(87) PCT Pub. No.: WO2016/024225
PCT Pub. Date: Feb. 18, 2016

(65) Prior Publication Data
US 2017/0253599 A1    Sep. 7, 2017

(30) Foreign Application Priority Data
Aug. 11, 2014 (IN) ............... 2287/DEL/2014

(51) Int. Cl.
*C07D 471/00* (2006.01)
*C07D 487/00* (2006.01)
*C07D 491/00* (2006.01)
*C07D 487/04* (2006.01)

(52) U.S. Cl.
CPC .................. *C07D 487/04* (2013.01)

(58) Field of Classification Search
CPC ................................... C07D 487/04
USPC ........................................ 544/254
See application file for complete search history.

(56) References Cited

U.S. PATENT DOCUMENTS

2007/0293513 A1    12/2007    Bohlin et al. ............ 514/261.1

FOREIGN PATENT DOCUMENTS

| IN | 1498/MUM/2012 | 1/2014 | .......... C07D 239/48 |
| WO | WO 01/92262 | 12/2001 | .......... C07D 487/04 |
| WO | WO2013/150495 | * 10/2013 | .......... C07D 487/04 |
| WO | WO 2013/150495 | 10/2013 | .......... C07D 487/04 |
| WO | WO 2014/006091 | 1/2014 | .......... C07D 487/04 |
| WO | WO 2014/083139 | 6/2014 | .......... C07D 487/04 |
| WO | WO2014/195861 | * 12/2014 | .......... C07D 487/04 |

OTHER PUBLICATIONS http://ccc.chem.pitt.edu/wipf/Web/Crystallization%20Solvents.pdf, last accessed Aug. 15, 2017.*
*Amorphous Forms of (1S, 2S, 3R, 5S)-3-[7-[[(1R,2S)-2-(3,4-difluorophenyl)cyclopropyl]amino]-5-(propylthio)-3H-1,2,3-triazolo[4,5,d]pyrimidine-3-yl]-5-(2-hydroxyethoxy)-,2-cyclopentandiol*, published Jun. 15, 2011 on website IP.com as Prior Art Database Disclosure No. IPCOM000207885D.
Co-pending PCT Application No. PCT/IB2015/056117 filed Aug. 11, 2015.
International Search Report and Written Opinion for International Application No. PCT/IB2015/056117, issued by ISA/US dated Dec. 10, 2015.
International Preliminary Report on Patentability for PCT/IB2015/056117 filed Aug. 11, 2015, issued by WIPO dated Feb. 23, 2017.

* cited by examiner

*Primary Examiner* — Jeffrey H Murray

(57) ABSTRACT

The present invention relates to a stable amorphous ticagrelor and a process for its preparation.

6 Claims, 1 Drawing Sheet

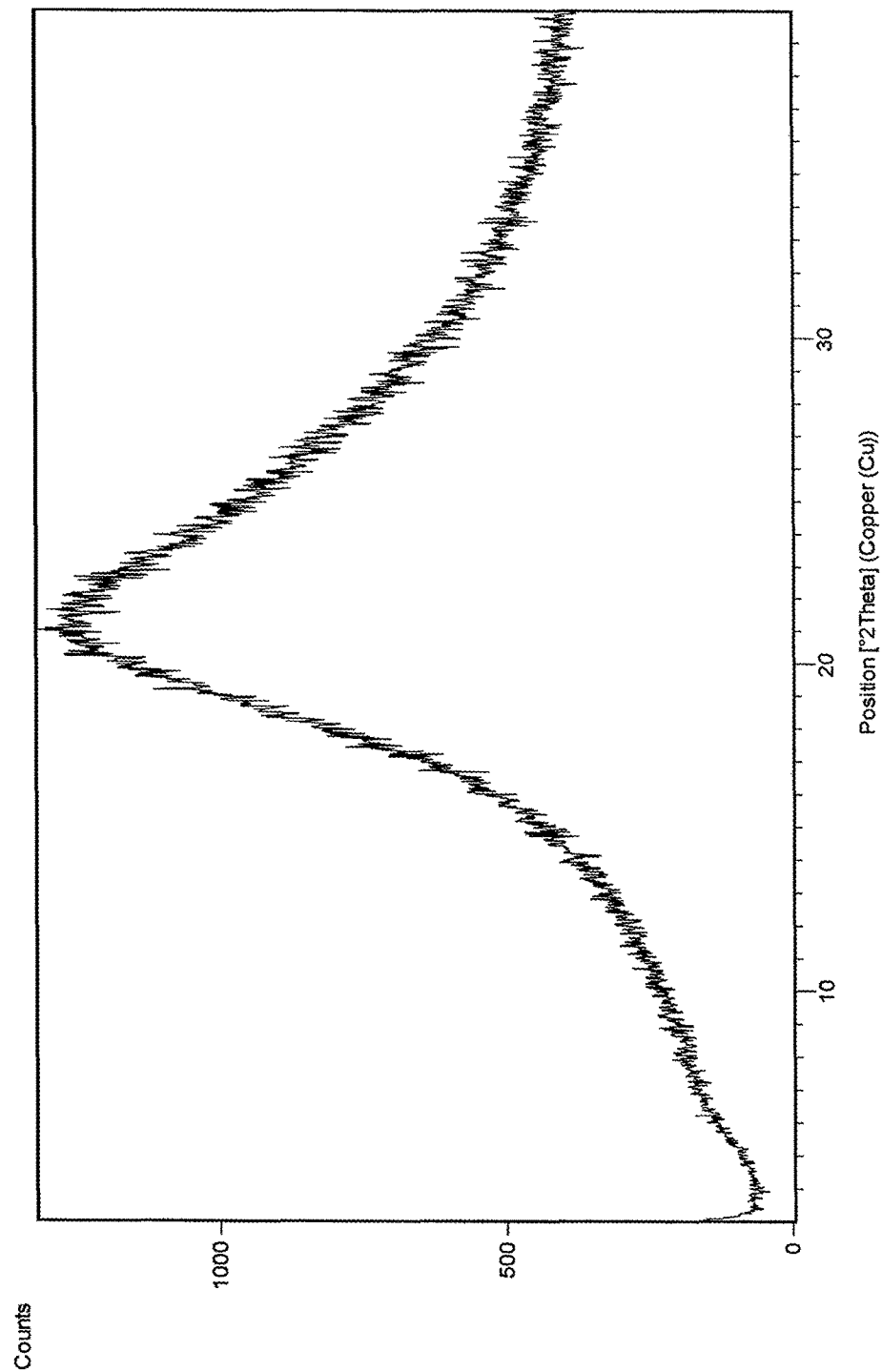

STABLE AMORPHOUS TICAGRELOR AND A PROCESS FOR ITS PREPARATION

FIELD OF THE INVENTION

The present invention relates to a stable amorphous ticagrelor and a process for its preparation.

BACKGROUND OF THE INVENTION

Ticagrelor, chemically (1S,2S,3R,5S)-3-[7-{[(1R,2S)-2-(3,4-difluorophenyl)cyclopropyl]amino}-5-(propylthio)-3H-[1,2,3]-triazolo[4,5-d]pyrimidin-3-yl]-5-(2-hydroxyethoxy)cyclopentane-1,2-diol, is represented by Formula I.

Formula I

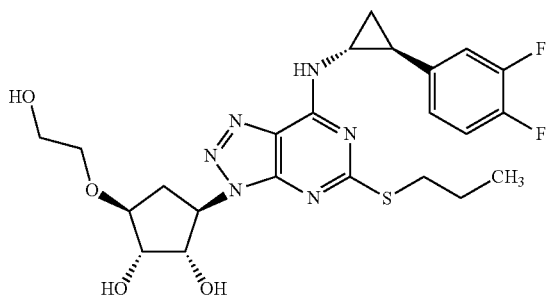

Ticagrelor is indicated to reduce the rate of thrombotic cardiovascular events in patients with acute coronary syndrome (ACS) (unstable angina, non-ST elevation myocardial infarction, or ST elevation myocardial infarction).

PCT Publication No. WO 01/92262 provides a process for the preparation of an amorphous ticagrelor using a freeze drying technique in an aqueous ethanolic solution of ticagrelor.

IPCOM000207885D describes the use of spray drying, evaporation, quenching, and grinding techniques for the preparation of an amorphous ticagrelor.

PCT Publication No. WO 2014/006091 describes a process for the preparation of an amorphous ticagrelor by dissolving ticagrelor in aqueous ethanol with the aid of ultrasonic irradiation, followed by the addition of water to obtain a turbid mixture. The turbid mixture is frozen immediately in liquid nitrogen to obtain a material, which is lyophilized to get the amorphous ticagrelor.

Indian Patent Application No. 1498/MUM/2012 describes a process for the preparation of an amorphous ticagrelor by dissolving ticagrelor in a mixture of acetonitrile and water, and isolating the amorphous ticagrelor by distillation under reduced pressure.

PCT Publication No. WO 2014/083139 describes a process for the preparation of an amorphous ticagrelor by dissolving ticagrelor in methanol and isolating the amorphous ticagrelor by the evaporation of the methanol under vacuum.

There is still a need in the art to develop a commercially viable process for the preparation of a stable amorphous ticagrelor.

SUMMARY OF THE INVENTION

The present invention relates to a stable amorphous ticagrelor and a process for its preparation.

BRIEF DESCRIPTION OF THE DRAWING

FIG. 1 depicts the X-ray powder diffraction (XRPD) pattern of an amorphous ticagrelor.

DETAILED DESCRIPTION OF THE INVENTION

The term "about," as used herein, refers to any value which lies within the range defined by a number up to ±10% of the value.

The term "stable amorphous ticagrelor," as used herein, refers to the amorphous ticagrelor for which no change was observed in an X-ray powder diffraction (XRPD) pattern when placed at a temperature of 25° C.±2° C. at a relative humidity of 60% ±5% for 1, 2, 3, and 6 months, and at a temperature of 5° C.±3° C. for 3 and 6 months.

A first aspect of the present invention provides a process for the preparation of a stable amorphous ticagrelor comprising:
a) dissolving ticagrelor in a solvent selected from the group consisting of chlorinated hydrocarbons, esters, cyclic ethers, and mixtures thereof to form a solution; and
b) adding the solution of step a) to a hydrocarbon solvent to obtain the stable amorphous ticagrelor.

The ticagrelor used for the preparation of the stable amorphous ticagrelor of the present invention may be in any polymorphic form, for example, crystalline Forms I, II, III, or IV, and may be prepared according to the methods provided in the art, for example, PCT Publication No. WO 01/92262.

Examples of chlorinated hydrocarbons include dichloromethane, dichloroethane, and chloroform.

An example of an ester is ethyl acetate.

Examples of cyclic ethers include tetrahydrofuran and dioxane.

The solution of ticagrelor is added to the hydrocarbon solvent and the reaction mixture is stirred at a temperature of from about −10° C. to about 15° C., for example, from about −5° C. to about 10° C., for about 45 minutes to about 6 hours, for example, for about 1 hour to about 4 hours.

Examples of hydrocarbon solvents include n-pentane, n-hexanes, n-heptane, and cyclohexane.

The isolation of the stable amorphous ticagrelor from the reaction mixture may be carried out by cooling, precipitation, washing, filtration, or combinations thereof. The stable amorphous ticagrelor may further be dried by using known methods, for example, drying under reduced pressure, vacuum drying, or air drying.

The stable amorphous ticagrelor prepared by the process of the present invention shows no change in XRPD pattern when it is placed at a temperature of 25° C.±2° C. at relative humidity of 60% ±5% for 1, 2, 3, and 6 months, and at a temperature of 5° C.±3° C. for 3 and 6 months.

A second aspect of the present invention provides a stable amorphous ticagrelor.

While the present invention has been described in terms of its specific aspects and embodiments, certain modifications and equivalents will be apparent to those skilled in the art, and are intended to be included within the scope of the present invention.

Methods

The X-ray powder diffraction (XRPD) pattern was recorded using a PANalytical® X'pert PRO with X'celerator® as the detector.

EXAMPLES

Example 1

Preparation of an Amorphous Ticagrelor

Ticagrelor (0.5 g) was dissolved in dichloromethane (17 mL) by heating at 40° C. to obtain a solution. The solution was added to precooled n-heptane (125 mL) at 0° C. to 5° C. The reaction mixture was stirred at 0° C. to 5° C. for 2 hours to obtain a precipitate. The precipitate was filtered, and then dried under vacuum at 25° C. to 30° C. for 4 hours to obtain the amorphous ticagrelor.
Yield: 0.28 g

Example 2

Preparation of an Amorphous Ticagrelor

Ticagrelor (5 g) was dissolved in dichloromethane (100 mL) at 40° C. to 45° C. to obtain a solution. The solution was added to precooled n-heptane (730 mL) at 0° C. to 5° C. The reaction mixture was stirred at 0° C. to 5° C. for 2 hours to obtain a precipitate. The precipitate was filtered, and then dried under vacuum at 25° C. to 30° C. for 8 hours to obtain the amorphous ticagrelor.
Yield: 3 g

Example 3

Preparation of an Amorphous Ticagrelor

Ticagrelor (25 g) was dissolved in dichloromethane (487.5 mL) and tetrahydrofuran (12.5 mL) at 40° C. to 45° C. to obtain a solution. The solution was distilled to recover the dichloromethane (250 mL). The solution was added to precooled n-heptane (2500 mL) at 0° C. to 5° C. over a period of 2 hours to 3 hours. The resultant slurry was stirred at 0° C. to 5° C. for 2 hours to obtain a precipitate. The precipitate was filtered, then washed with n-heptane (100 mL), and then dried under vacuum at 25° C. to 30° C. for 6 hours to obtain the amorphous ticagrelor.
Yield: 22 g

Example 4

Preparation of an Amorphous Ticagrelor

Ticagrelor (2 g) was dissolved in dichloromethane (10 mL) and tetrahydrofuran (2 mL) to obtain a solution. The solution was added to precooled n-heptane (96 mL) at 0° C. to 5° C. The resultant slurry was stirred for 2 hours at 0° C. to 5° C. to obtain a precipitate. The precipitate was filtered, and then dried under vacuum at 25° C. to 30° C. to obtain the amorphous ticagrelor.
Yield: 1.5 g

Example 5

Preparation of an Amorphous Ticagrelor

Ticagrelor (0.5 g) was dissolved in ethyl acetate (4 mL) by heating at 65° C. to obtain a solution. The solution was added to pre-cooled cyclohexane (50 mL) at 0° C. to 5° C. The reaction mixture was cooled to 0° C. to 5° C. for 3 hours, then filtered, and then dried under vacuum at 25° C. to 30° C. for 2 hours to obtain the amorphous ticagrelor.
Yield: 0.25g

Example 6

Preparation of an Amorphous Ticagrelor

Ticagrelor (2 Kg) was dissolved in dichloromethane (40 L) and tetrahydrofuran (1 L) at 40° C. to 45° C. to obtain a solution. The solution was distilled to recover the dichloromethane (20 L). The solution was added to precooled n-heptane (200 L) at 0° C. to 5° C. over a period of 2 hours to 3 hours. The reaction mixture was stirred at 0° C. to 5° C. for 2 hours to obtain a precipitate. The precipitate was filtered, then washed with n-heptane (20 L), and then dried under vacuum at 30° C. to 35° C. for 6 hours to obtain the amorphous ticagrelor.
Yield: 1.82 Kg HPLC purity (initial and at stability at a temperature of 25° C.±2° C. at relative humidity of 60% ±5% for 1, 2, 3, and 6 months): 99.8%

HPLC purity (initial and at stability at a temperature of 5° C.±3° C. for 3 and 6 months): 99.9%

When amorphous ticagrelor was placed at a temperature of 25° C.±2° C. at a relative humidity of 60% ±5% for 1, 2, 3, and 6 months, and at a temperature of 5° C.±3° C. for 3 and 6 months, no change was observed in the XRPD pattern, showing that the amorphous ticagrelor obtained by following the present invention is stable.

We claim:

1. A process for the preparation of a stable amorphous ticagrelor comprising:
    a) dissolving ticagrelor in a solvent selected from dichloromethane, tetrahydrofuran, and mixtures thereof to form a solution; and
    adding the solution of step a) to n-heptane to obtain the stable amorphous ticagrelor.

2. The process of claim 1, wherein the stable amorphous ticagrelor shows no change in XRPD pattern when it is placed at a temperature of 25° C±2° C. at relative humidity of 60% ±5% for 1, 2, 3, and 6 months, and at a temperature of 5° C.±3° C. for 3 and 6 months.

3. The process of claim 1, wherein the ticagrelor is dissolved in a solvent at a temperature of 40° C to 65° C.

4. The process of claim 3, wherein the ticagrelor dissolved in the solvent is added to the n-heptane precooled to 0° C to 5° C.

5. The process of claim 4, wherein the ticagrelor dissolved in the hydrocarbon solvent at a temperature of 0° C to 5° C is further stirred for about two hours to three hours to obtain a precipitate.

6. The process of claim 5, wherein the precipitate is dried under vacuum at a temperature of 25° C to 35° C to obtain the amorphous ticagrelor.

* * * * *